(12) United States Patent
Wang et al.

(10) Patent No.: US 12,069,995 B2
(45) Date of Patent: Aug. 27, 2024

(54) PNEUMATIC POLLINATION DEVICE FOR HYBRID RICE SEED PRODUCTION WITH LARGE ROW RATIO AND METHOD THEREFOR

(71) Applicant: ZHEJIANG UNIVERSITY, Hangzhou (CN)

(72) Inventors: Yongwei Wang, Hangzhou (CN); Fuqiang Yao, Hangzhou (CN); Jun Wang, Hangzhou (CN); Zhenbo Wei, Hangzhou (CN); Shaoming Cheng, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 663 days.

(21) Appl. No.: 17/340,098

(22) Filed: Jun. 7, 2021

(65) Prior Publication Data
US 2021/0289728 A1    Sep. 23, 2021

Related U.S. Application Data

(63) Continuation of application No. PCT/CN2020/122125, filed on Oct. 20, 2020.

(51) Int. Cl.
*A01H 1/02* (2006.01)
(52) U.S. Cl.
CPC .................................. *A01H 1/027* (2021.01)
(58) Field of Classification Search
CPC . A01H 1/027; A01H 1/02; A01G 7/06; A01G 17/005; A01G 17/00; A01G 22/40
See application file for complete search history.

(56) References Cited

FOREIGN PATENT DOCUMENTS

| CN | 102812900 A | 12/2012 |
| CN | 202958391 U | 6/2013 |
| CN | 103250629 A | 8/2013 |
| CN | 103250630 A | 8/2013 |
| CN | 103250631 A | 8/2013 |
| CN | 103262786 A | 8/2013 |
| CN | 203279612 U | 11/2013 |
| CN | 106258943 A | 1/2017 |
| CN | 110214690 A | 9/2019 |

(Continued)

OTHER PUBLICATIONS

International Search Report (PCT/CN2020/122125); Date of Mailing: Jan. 21, 2021.

*Primary Examiner* — Trinh T Nguyen
(74) *Attorney, Agent, or Firm* — W&G Law Group

(57) ABSTRACT

A pneumatic pollination device and a method for hybrid rice seed production with a large row ratio are provided. The pneumatic pollination device includes a pneumatic pollination component, a controller, a lifting adjustment component and a four-wheel power chassis. The pneumatic pollination component is mounted at the front part of the four-wheel power chassis through the lifting adjusting component, and the controller is mounted at the upper part of the four-wheel power chassis. The airflow of each pollination pipe respectively acts on the spike part of the male parent row of corresponding hybrid rice, so that the male pollen is separated from stamens and floats to the female compartment. The airflow velocities of the pollination pipes of respective male parent rows are different to ensure that the pollen is conveyed to the main female parent action region.

8 Claims, 3 Drawing Sheets

(56) References Cited

FOREIGN PATENT DOCUMENTS

| CN | 111165345 | A |   | 5/2020  |          |
|----|-----------|---|---|---------|----------|
| CN | 111248081 | A | * | 6/2020  | A01H 1/02 |
| CN | 116724885 | A | * | 9/2023  |          |
| CN | 117730770 | A | * | 3/2024  |          |
| WO | 2018129302 | A1 |  | 7/2018  |          |

* cited by examiner

PNEUMATIC POLLINATION DEVICE FOR HYBRID RICE SEED PRODUCTION WITH LARGE ROW RATIO AND METHOD THEREFOR

CROSS-REFERENCE TO RELATED APPLICATIONS

The present application is a continuation of International Application No. PCT/CN2020/122125, which claims priority to Chinese Patent Application No. 202010121685.0, each of which is incorporated by reference in its entirety.

TECHNICAL FIELD

The present application relates to a mechanized pollination device for hybrid rice seed production in the field, in particular to a pneumatic pollination device with a large row ratio of male and female parents and a method thereof which are suitable for large-scale seed production.

BACKGROUND

Hybrid rice seeds are the material basis of hybrid rice production, but rice is a self-pollinated plant, and the natural hybridization rate in the natural environment is generally only 0.2%-0.3%. To keep the hybrid advantage of seeds, we can only use "manual pollination" to ensure full and even pollination, increase the outcrossing maturing rate and improve the yield and quality of seed production. Pollen flowering time of rice is only 7-10 days, and the bloom time is only about 2-4 hours a day, so pollination must be completed within a limited time.

At present, there is no suitable pollination machinery and equipment in China. Pollination is still completed by traditional "manpower" pollination, such as single-long-rod powder-pushing, double-short-rod powder pushing and rope powder pulling. Single-long-rod powder-pushing and double-short-rod powder-pushing are only suitable for small-scale seed production in families with row ratios of 1:3, 1:4, 2:6 and 2:8 for male and female parents. The productivity is extremely low, and only 0.2-0.3 hectares can be pollinated per hour. However, the pollination operation period is short and needs a lot of labor to complete, which cannot meet the requirements of large-scale production of modern seed industry at all. Although the productivity of rope milling is slightly higher, there are some problems, such as high labor intensity, low utilization rate of pollen, serious plant damage to the plants and large yield loss. In recent years, attempts have been made in China and foreign countries to use micro unmanned aerial vehicles for pollination. However, due to the fact that the main body of airflow under the helicopter rotor is "vertical", it is not conducive to pollen spreading to the female parent, and the pollination rate cannot meet the requirements of seed production and pollination. In addition, at present, the row ratio of male to female parents in hybrid rice seed production is small row ratio such as 1:3, 1:4, 2:6, 2:8, which is not conducive to the mechanized operation of multiple operations stages including pollination. Seed production agronomy with a large ratio such as 6:20, 6:24, 8:32 needs to be used to realize the mechanized production, but there is no technology and equipment that can realize the directional and uniform pollination of pollen. Therefore, at present, there is a need for a device for hybrid rice seed production and pollination with a large row ratio capable of mechanized and intelligent operation, which can greatly improve the pollination productivity, improves the mechanization level, seed production quality and yield of hybrid rice seed production, effectively solves the problems of machine substitution and labor shortage, and promotes the sustainable and healthy development of the seed industry.

SUMMARY

The present application aims to solve the problem of lack of mechanized pollination equipment in hybrid rice seed production at present, to meet the needs of large-scale seed production, and provides a pneumatic pollination device for hybrid rice seed production with a large row ratio, which realizes directional, uniform and efficient pollination through each pollinator acting on different female parent areas.

The technical solution adopted by the present application to solve the technical problems is as follows:

A pneumatic pollination device for hybrid rice seed production with a large row ratio includes a pneumatic pollination component, a controller, a lifting adjustment component and a four-wheel power chassis; wherein, the pneumatic pollination component is mounted at a front part of the four-wheel power chassis through the lifting adjustment component, the lifting adjustment component controls up-and-down lifting, and the controller is mounted at an upper part of the four-wheel power chassis;

the pneumatic pollination component includes a lifting frame, five airflow velocity sensors, a left side one-way pollination pipe, a left middle one-way pollination pipe, a central pollination pipe, a right middle one-way pollination pipe, a right side one-way pollination pipe, five blowers, five supporting plates, five motor drivers and a storage battery;

the left side one-way pollination pipe and the left middle one-way pollination pipe are both L-shaped, and each of front parts of horizontal sections of the left side one-way pollination pipe and the left middle one-way pollination pipe is provided with an air blowing port on a side facing away from the central pollination pipe and a guide plate horizontally fixed below the air blowing port, and a base configured to install one of the five airflow velocity sensors is arranged at each of middle and lower parts of vertical sections of the left side one-way pollination pipe and the left middle one-way pollination tube at a same height; the right side one-way pollinate pipe and the right middle one-way pollinating pipe are arranged in a mirror symmetrical structure with respect to the left side one-way pollinate pipe and the left middle one-way pollinating pipe, respectively;

wherein the central pollination pipe is also L-shaped, a front part of a horizontal section of the central pollination pipe is provided with two air blowing port at both sides of the front part, and the guide plate is horizontally fixed below each of the two air blowing ports of the central pollination pipe; a middle and lower part of a vertical section of the central pollination pipe is provided with the base that is configured to install one of the five airflow velocity sensors, and an installation height of the base of the central pollination pipe is consistent with installation heights of the bases on the other pollination pipes;

wherein a rear part of a vertical part of each pollination pipe is provided with two L-shaped sliding sleeves, a distance between the two L-shaped sliding sleeves is consistent with a height of the lifting frame, and a locking bolt is arranged at an outer side of each of the two sliding sleeves; each pollination pipe is clamped and mounted at a front part of the lifting frame through the two L-shaped sliding sleeves and locked and fixed by the locking bolts, and lower parts of the horizontal sections of respective pollination pipes are located on a same horizontal plane;

wherein the five supporting plates are distributed and fixed at a rear upper part of a bracket, and one of the five blowers are fixed at a side of a respective one of the five supporting plates, and air inlets of the left side one-way pollination pipe, the left middle one-way pollination pipe, the central pollination pipe, the right middle one-way pollination pipe and the right side one-way pollination pipe are respectively connected with the five blowers through hoses;

wherein the five airflow velocity sensors are respectively fixed on the bases of vertical pipes of the left side one-way pollination pipe, the left middle one-way pollination pipe, the central pollination pipe, the right middle one-way pollination pipe and the right side one-way pollination pipe, and a measuring point of one of the five airflow velocity sensors extends to a center of the pollination pipe where the airflow velocity sensor is located; and wherein the storage battery is fixed on the four-wheel power chassis, the five motor drivers for airflow control are respectively fixed on the sides of the five supporting plates, a power input end of each of the five motor drivers is connected with the storage battery through a cable, and a power output end of each of the five motor drivers are connected with one of the five blowers through a cable; and control ends of the five motor drivers are connected with the controller through control cables.

Another object of the present application is to provide a pollination method using the pneumatic pollination device for hybrid rice seed production with a large row ratio, including:

adjusting distribution of the pollination pipes: adjusting a horizontal position of the central pollination pipe on the lifting frame, in such a manner that a longitudinal center of the central pollination pipe and a longitudinal center of the pneumatic pollination device for hybrid rice seed production with a large row ratio are located on a same vertical plane, and then fixing the central pollination pipe to the lifting frame through the locking bolts on the sliding sleeves; transversely and horizontally adjusting the left side one-way pollination pipe, the left middle one-way pollination pipe, the right middle one-way pollination pipe and the right side one-way pollination pipe based on a planting row spacing of male parents in such a manner that spacings of adjacent central lines of horizontal sections of the left side one-way pollination pipe, the left middle one-way pollination pipe, the central pollination pipe, the right middle one-way pollination pipe and the right side one-way pollination pipe are respectively consistent with five row spacings corresponding to six rows of the male parents of hybrid rice in a seed production field, and then fixing each of the pollination pipes to the lifting frame by the locking bolts on the sliding sleeves;

moving the pneumatic pollination device to the seed production field: before 10:00 AM of a day during full bloom of the male parents of hybrid rice, driving the pneumatic pollination device for hybrid rice seed production with a large row ratio to the seed production field in such a manner that four walking driving wheels of the pneumatic pollination device straddle the six rows of male parents, wherein the four walking driving wheels are located between ridges of adjacent male and female parents of hybrid rice, and a horizontal section of the central pollination pipe is located between ridges of two rows of the male parents at the utmost center among the six rows of male parents;

adjusting a height of the pneumatic pollination component: controlling, by the controller, the stepping motor to operate, the stepping motor driving a screw rod to rotate, and the screw rod driving the lifting frame to move up and down so as to drive the five pollination pipes to move up and down synchronously, and stopping movement of the five pollination pipes when the air blowing ports of the five pollination pipes reach the middle and lower parts of a spike region of the male parents;

adjusting airflow parameters of the pollination pipes: based on a requirement for pollination airflow velocity for a row of male parents of a current breed of hybrid rice, setting, by the controller, airflow velocities at the air blowing ports of the left side one-way pollination pipe, the left middle one-way pollination pipe, the central pollination pipe, the right middle one-way pollination pipe and the right side one-way pollination pipe, and then controlling, by the controller, the five motor drivers to drive the five blowers to operate, and outputting airflow at the air blowing ports of each of the pollination pipes at a preset wind speed;

pollinating field: during a period from 10:30 AM to 2:30 PM of a day when the male parents of hybrid rice are in full bloom, after adjusting the airflow parameters of the pollination pipes, the pneumatic pollination device for hybrid rice seed production with a large row ratio straddling six rows of the male parents of hybrid rice and advancing along a center line at a specified speed, the left side one-way pollination pipe, the left middle one-way pollination pipe, the central pollination pipe, the right middle one-way pollination pipe and the right side one-way pollination pipe respectively being located between rows of the six rows of male parents of hybrid rice, blowing airflow from the air blowing ports of the left side one-way pollination pipe and the left middle one-way pollination pipe to spike parts of the left two rows of the male parents, blowing airflow from the air blowing ports of the right middle one-way pollination pipe and the right side one-way pollination pipe to spike parts of the right two rows of the male parents, and blowing airflow from the air blowing ports of the two sides of the central pollination pipe to spike parts of the central two rows of the male parents respectively; pollens of the male parents being separated from flower cores and floating with the airflow under the action of airflow and spike swing, pollens of the left three rows of male parents floating to the left adjacent row of female parents under the action of left-ward airflow, and pollens of the right three rows of male parents floating to the right adjacent row of female parents under the action of right-ward airflow; with the gradual decrease of the airflow velocity above a female parent compartment, pollens settling down under the action of gravity, and part of the pollens settling on the spike parts of the female parents to realize pollination; when the pneumatic pollination device for hybrid rice seed production with a large row ratio travels to an end point of the six rows of male parents in the compartment, the pneumatic pollination device turning around in the field to the six rows of the male parents in another adjacent compartment to continue pollination; and the pneumatic pollination device traveling to each male parent compartment in turn for pollination, and performing pollination 2-3 times a day from 10:30 to 14:30 during the full bloom; and stopping maintenance: after pollination is finished every day, firstly controlling, by the controller, the motor driver to stop the five blowers, and then driving the pneumatic pollination device for hybrid rice seed production with a large row ratio to an agricultural machinery warehouse for maintenance, so as to prepare for pollination of the next day.

The method has the beneficial effects that the male parent pollen of hybrid rice is separated from the stamens and floats to the female parent compartment by directional and uniform airflow, and the different airflow velocities acting on the pollination pipes of each male parent row can transport the pollen to the main acting female parent areas, thereby realizing the directional floating and uniform pollination of the pollen in large-scale seed production and providing a working device for mechanized and efficient pollination of hybrid rice seed production.

Figure 1:
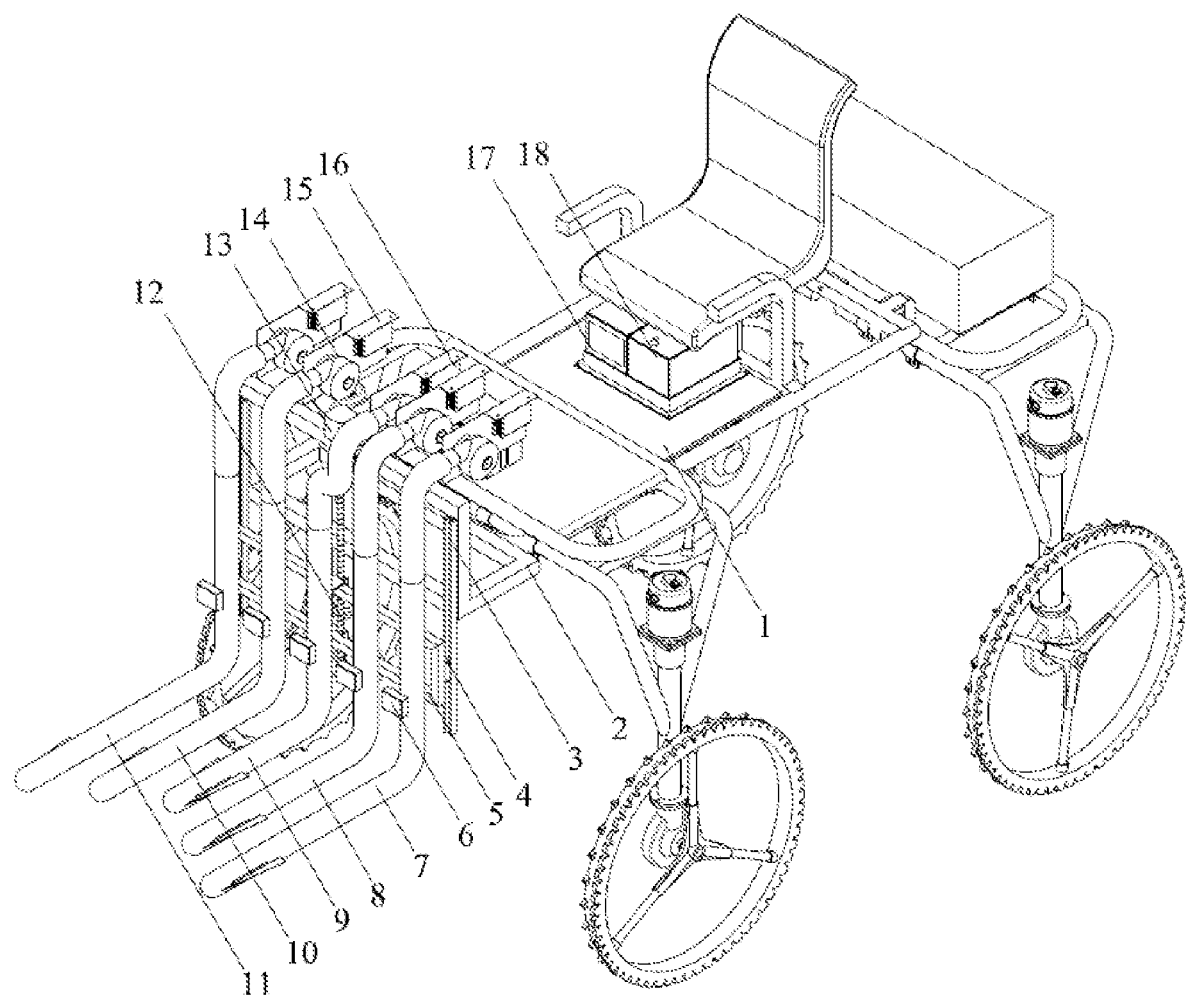
FIG. 1 is a three-dimensional structure diagram of a pneumatic pollination device for large-scale hybrid rice seed production.

In the drawing: four-wheel power chassis 1, bracket 2, lifting guide rail 3, sliding block 4, lifting frame 5, airflow velocity sensor 6, left side one-way pollination pipe 7, left middle one-way pollination pipe 8, central pollination pipe 9, right middle one-way pollination pipe 10, right side one-way pollination pipe 11, screw rod 12, stepping motor 13, blower 14, supporting plate 15, motor driver 16, controller 17, storage battery 18, ball nut 19, sliding sleeve 20, air blowing port 21, guide plate 22, base 23.

DESCRIPTION OF EMBODIMENTS

The present application will be further explained with reference to drawings and examples.

As shown in FIGS. 1-4, it is a pneumatic pollination device for hybrid rice seed production with large ratio in the present application, and its main components include a pneumatic pollination component, a controller 17, a lifting adjustment component and a four-wheel power chassis 1; wherein, the pneumatic pollination component is mounted at a front part of the four-wheel power chassis 1 through the lifting adjustment component, the lifting adjustment component controls up-and-down lifting, and the controller 17 is mounted at an upper part of the four-wheel power chassis 1 for controlling the work of each component in the pneumatic pollination device for hybrid rice seed production with a large row ratio.

As shown in FIG. 1, the pneumatic pollination component includes a lifting frame 5, an airflow velocity sensor 6, a left side one-way pollination pipe 7, a left middle one-way pollination pipe 8, a central pollination pipe 9, a right middle one-way pollination pipe 10, a right side one-way pollination pipe 11, a blower 14, supporting plates 15, a motor driver 16 and a storage battery 18.

Figure 2:
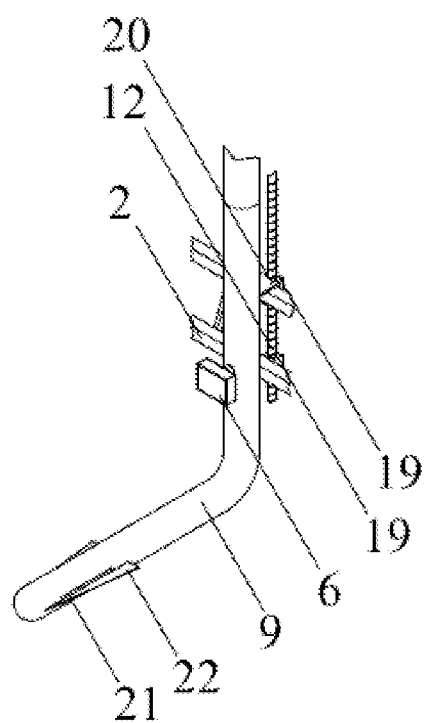
FIG. 2 is a schematic diagram of the assembly structure of the ball nut, the sliding sleeve, the screw rod and the bracket.
Figure 3:
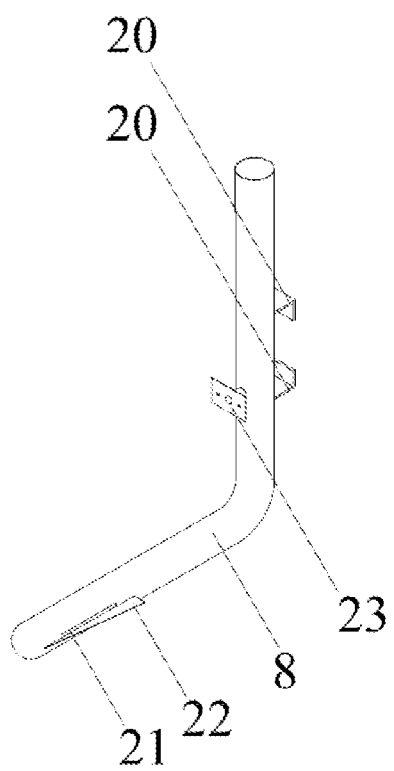
FIG. 3 is a three-dimensional structure diagram of the left middle one-way pollination pipe.

The left side one-way pollination pipe 7 and the left middle one-way pollination pipe 8 are both L-shaped, their basic mechanisms are basically the same, and they are formed by connecting vertical sections and horizontal sections. FIG. 3 shows the structure of the left middle one-way pollination pipe 8. The front parts of horizontal sections of the left side one-way pollination pipe 7 and the left middle one-way pollination pipe 8 are provided with air blowing ports 21 on a side facing away from the central pollination pipe 9, a guide plate 22 is horizontally fixed below the air blowing ports, therefore, the left side one-way pollination pipe 7 and the left middle one-way pollination pipe 8 can form airflow blowing towards the left side, and the airflow direction can be adjusted by the angle of the guide plate 22. A base 23 for installing the airflow velocity sensor 6 is arranged at a same height at middle and lower parts of vertical sections of the left side one-way pollination pipe 7 and the left middle one-way pollination pipe 8. The right side one-way pollinate pipe 10 and that right middle one-way pollinating pipe 11 are in mirror image symmetrical structure with the left side one-way pollinate pipe 7 and the left middle one-way pollinating pipe 8 respectively. The mirror symmetry plane is the central vertical plane of the central pollination pipe 9. The air blowing ports 21 on the right side one-way pollination pipe 10 and the right middle one-way pollination pipe 11 are also located on the side away from the central pollination tube 9, so they can form an airflow blowing toward the right side. As shown in FIG. 2, the central pollination pipe 9 is also L-shaped, and a front part of the horizontal section of the central pollination pipe 9 is provided with air blowing ports 21 facing both sides, and a guide plate 22 is horizontally fixed below the air blowing ports 21; middle and lower part of a vertical section of the central pollination pipe 9 is provided with the base 23 for installing the airflow velocity sensor 6, and the installation height of the base 23 is consistent with that of bases 23 on other pollination pipes. In this embodiment, among the five pollination pipes, the air blowing port 21 is a slit for blowing out the airflow in the pipes; each of the air blowing ports 21 is arranged on the horizontal center plane of the horizontal section of the pollination pipe where it is located, and the so-called horizontal center plane is the horizontal plane passing through the horizontal diameter of the cross section of the pollination pipe.

The rear part of a vertical part of each pollination pipe is provided with two L-shaped sliding sleeves 20, a distance between the two L-shaped sliding sleeves 20 is consistent with a height of the lifting frame 5 so that it can be clamped on the lifting frame 5.

The locking bolt is arranged outside the sliding sleeves 20, each pollination pipe is clamped and mounted at a front part of the lifting frame 5 through two L-shaped sliding sleeves 20 and locked and fixed by the locking bolt, and lower parts of the horizontal sections of respective pollination pipes are on a same horizontal plane. The relative position of the pollination pipe on the lifting frame 5 can be adjusted transversely, and after the pollination pipe moves to the target position on the lifting frame 5, it can be fixed by tightening the locking bolt.

Five supporting plates 15 are distributed and fixed on a rear upper part of a bracket 2, and five blowers 14 are respectively fixed on sides of the supporting plates 15; air inlets of the left side one-way pollination pipe 7, the left middle one-way pollination pipe 8, the central pollination pipe 9, the right middle one-way pollination pipe 10 and the right side one-way pollination pipe 11 are respectively connected with one blower 14 through a hose. The connection is also one-to-one correspondence, and the hose can ensure that the pollination pipe has a certain lateral moving space. Each pollination pipe can control the airflow at its air blowing port 21 by the blower 14.

Five airflow velocity sensors 6 are respectively fixed on the bases 23 of vertical pipes of the left side one-way pollination pipe 7, the left middle one-way pollination pipe 8, the central pollination pipe 9, the right middle one-way pollination pipe 10 and the right side one-way pollination pipe 11, and a measuring point of the airflow velocity sensor 6 extends into a center of the pollination pipe where the airflow velocity sensor 6 is located to detect the airflow inside the pollination pipe in real time.

The storage battery 18 is fixed on the four-wheel power chassis 1, five motor drivers 16 for airflow control are respectively fixed on the sides of the five supporting plates 15, a power input end of each motor driver 16 is connected with the storage battery 18 through a cable, and the motor driver 16 is powered by the storage battery 18. The output ends of the five motor drivers 16 are respectively connected with five blowers 14 through cables; the control ends of the five motor drivers 16 are connected with a controller 17 through control cables. At the same time, five airflow velocity sensors 6 can also be connected to the controller 17 to send the airflow data in the pollination pipe to the controller 17, so as to realize real-time control of the volume of the airflow.

Figure 4:
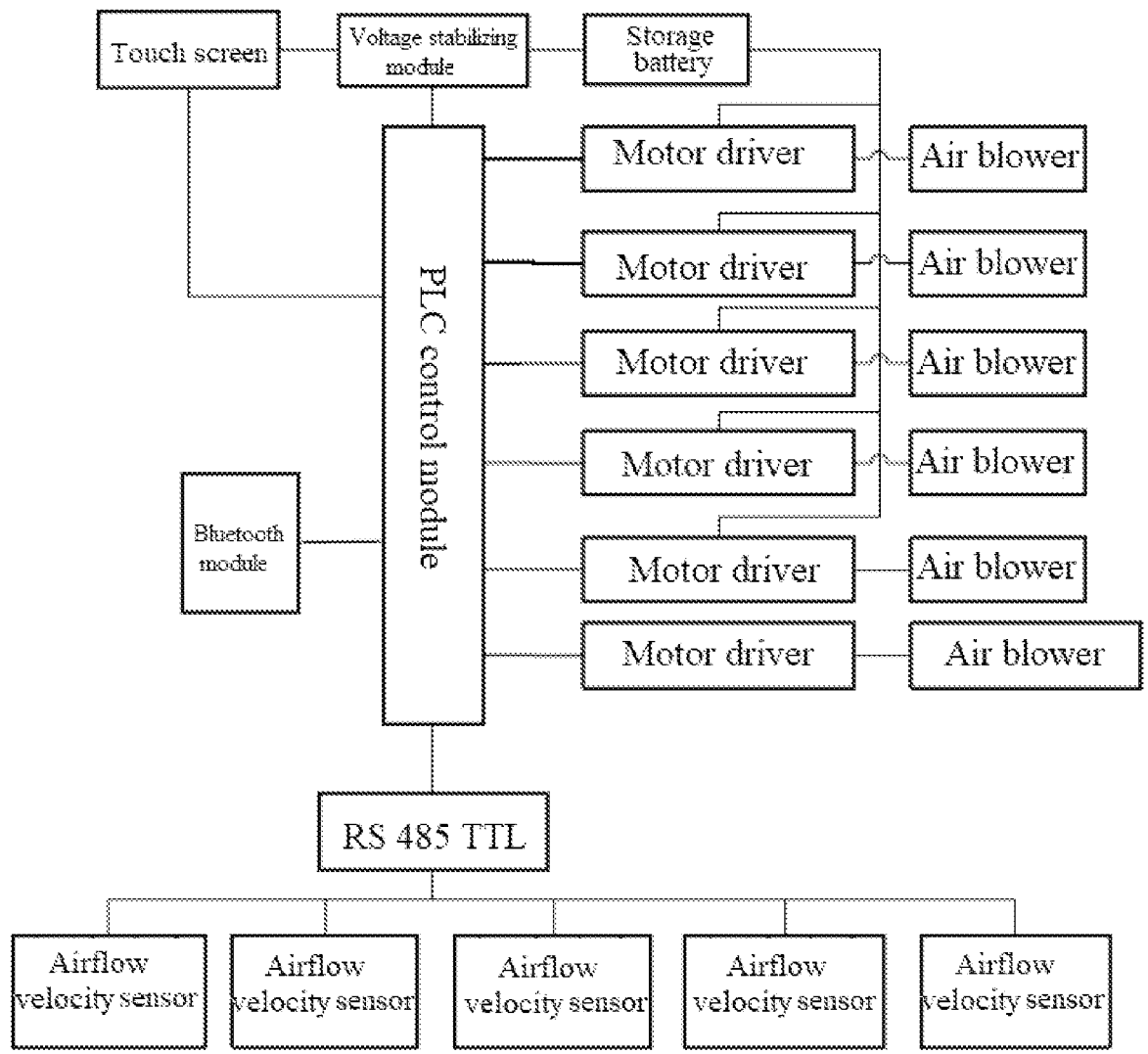
FIG. 4 is a block diagram of the composition principle of the controller.

In the present embodiment, the controller 17 is realized by a PLC control module, and its composition principle block diagram is shown in FIG. 4: the airflow velocity sensor 6 on each pollination pipe is connected with the PLC control module through a RS485 TTL module, a Bluetooth module and a touch screen are connected with the PLC control module, the storage battery 18 supplies power for the PLC control module and the touch screen through a voltage stabilizing module, the five motor drivers 16 are connected with the PLC control module through control lines, and the storage battery is connected with five motor drivers 16 through cables, while five motor drivers 16 are connected with five blowers 14 respectively. The Bluetooth module can be used for signal transmission with the outside. Specific parameter setting can be carried out through the touch screen for easy operation.

The lifting adjusting component in the application can be any equipment capable of adjusting the up and down height of the pneumatic pollination part. In this embodiment, the lifting adjustment component can be realized by a screw nut transmission device. Referring to FIG. 1, the lifting adjusting component includes a bracket 2, a lifting guide rail 3, a sliding block 4, a screw rod 12 and a stepping motor 13; the bracket 2 is used as the installation frame of the pneumatic pollination component, and its rear end is fixed at the front part of the four-wheel power chassis 1; two lifting guide rails 3 are respectively fixed on two sides of a front end of the bracket 2 along a vertical direction; each lifting guide rail 3 is provided with the sliding block 4 which forms a moving pair with the lifting guide rail 3, the rear part of the lifting frame 5 is mounted on the lifting guide rail 3 through the sliding block 4 and can move up and down with the sliding block 4; a ball nut 19 is fixed in the lifting frame 5, the middle and lower part of the screw rod 12 is installed in the middle of the lifting frame 5 through the ball nut 19, and the screw rod 12 and the ball nut 19 form a screw pair. The upper part of the screw rod 12 is mounted on a front upper middle part of the bracket 2 through a bearing, and the stepping motor 13 is fixed on the front upper middle part of the bracket 2; the upper end of the screw rod 12 is fixedly connected with the stepping motor 13, a central axis of the screw rod 12 is on the same line with an axis of a output shaft of the stepping motor 13. Thereby, the stepping motor 13 drives the screw rod 12 to rotate and drives the lifting frame 5 to move up and down. Further, the height of the pneumatic pollination component fixed on the lifting frame 5 is adjusted, so that the airflow blown by the pneumatic pollination component can blow to the spike part of the male parents with different heights.

In this embodiment, the vertical sections of the left side one-way pollination pipe 7, the left middle one-way pollination pipe 8, the central pollination pipe 9, the right middle one-way pollination pipe 10 and the right side one-way pollination pipe 11 have the same length; the horizontal sections of the five pollination pipes are on the same plane but have different lengths. In order to improve the effect of pneumatic pollination, the central connecting line of the front ends of the horizontal sections of the five pollination pipes in a V-shape which is concave towards the four-wheel power chassis 1, and the pollination pipes on both sides are longer, while the pollination pipe in the center is the shortest. Among the five pollination pipes, a length difference between the horizontal sections of two adjacent pollination pipes is 1-1.5 times of the length of the air blowing port 21.

In this embodiment, the guide plate 22 is triangular, and the tip of the guide plate 22 faces a heading direction of the pneumatic pollination device hybrid rice seed production with a large row ratio to reduce the damage to the spikes of rice in the process of traveling.

The pollination method using the pneumatic pollination device for hybrid rice seed production with a large row ratio includes the following steps:

a first step of adjusting distribution of pollination pipes: adjusting a horizontal position of a central pollination pipe 9 on a lifting frame 5, so that a longitudinal center of the central pollination pipe 9 and a longitudinal center of the pneumatic pollination device for hybrid rice seed production with a large row ratio are on a same vertical plane, and then fixing the central pollination pipe 9 with a lifting frame 5 through a locking bolt on a sliding sleeve 20; transversely and horizontally adjusting a left side one-way pollination pipe 7, a left middle one-way pollination pipe 8, a right middle one-way pollination pipe 10 and a right side one-way pollination pipe 11 according to a planting row spacing of male parents so that spacings of adjacent central lines of horizontal sections of the left side one-way pollination pipe 7, the left middle one-way pollination pipe 8, the central pollination pipe 9, the right middle one-way pollination pipe 10 and the right side one-way pollination pipe 11 are respectively consistent with five row spacings corresponding to six rows of the male parents of hybrid rice in a seed production field, and then fixing each pollination pipe with the lifting frame 5 by using the locking bolt on the sliding sleeve 20;

a second step of moving the device to the seed production field: before 10:00 when the male parents of hybrid rice are in full bloom, driving pneumatic pollination device for hybrid rice seed production with a large row ratio to the seed production field, so that four walking driving wheels of the device straddle the six rows of male parents, the walking driving wheels being located between ridges of adjacent male and female parents of hybrid rice, and a horizontal section of the central pollination pipe 9 being located between ridges of two rows of the male parents at the utmost center among the six rows of male parents;

a third step of adjusting a height of a pneumatic pollination component: controlling a stepping motor 13 to work by a controller 17, the stepping motor 13 driving a screw rod 12 to rotate, and the screw rod 12 driving the lifting frame 5 to move up and down so as to drive the five pollination pipes to move up and down synchronously, and stopping moving when the air blowing ports 21 of the five pollination pipes reach the middle and lower parts of a spike region of the male parents;

a fourth step of adjusting airflow parameters of the pollination pipe: according to a requirement for pollination airflow velocity for a row of male parents of a current breed of hybrid rice, the controller 17 setting airflow velocities at respective air blowing ports 21 of the left side one-way pollination pipe 7, the left middle one-way pollination pipe 8, the central pollination pipe 9, the right middle one-way pollination pipe 10 and the right side one-way pollination pipe 11, and then controlling a motor driver 16 by the controller 17 to make five blowers 14 work, and outputting airflow at the air blowing ports 21 of each pollination pipe at a set wind speed;

a fifth step of field pollination: when the male parents of hybrid rice are in full bloom from 10:30 AM to 2:30 PM of a day, after adjusting the airflow parameters of the pollination pipes, the pneumatic pollination device for hybrid rice seed production with a large row ratio straddling six rows of the male parents of hybrid rice and advancing along a center line at a specified speed, the left side one-way pollination pipe 7, the left middle one-way pollination pipe 8, the central pollination pipe 9, the right middle one-way pollination pipe 10 and the right side one-way pollination pipe 11 respectively being located between rows of the six rows of male parents of hybrid rice, airflow from the air blowing ports 21 of the left side one-way pollination pipe 7 and the left middle one-way pollination pipe 8 blowing to spike parts of the left two rows of the male parents, airflow from the air blowing ports 21 of the right middle one-way pollination pipe 10 and the right side one-way pollination pipe 11 blowing to spike parts of the right two rows of the male parents, and airflow from the air blowing ports 21 of the two sides of the central pollination pipe 9 blowing to spike parts of the central two rows of the male parents respectively; pollens of the male parents being separated from flower cores and floating with the airflow under the action of airflow and spike swing, pollens of the left three rows of male parents floating to the left adjacent row of female parents under the action of left-ward airflow, and pollens of the right three rows of male parents floating to the right adjacent row of female parents under the action of right-ward airflow; with the gradual decrease of the airflow velocity above a female parent compartment, pollens settling down under the action of gravity, and part of the pollens settling on the spike parts of the female parents to realize pollination; when the pneumatic pollination device for hybrid rice seed production with a large row ratio drives to an end point of the six rows of male parents in the compartment, the device turning around in the field to the six rows of the male parents in another adjacent compartment to continue pollination; and the device driving to each male parent compartment in turn for pollination, and carrying out pollination 2-3 times a day from 10:30 to 14:30 in full bloom;

a sixth step of stopping maintenance: after pollination is finished every day, firstly the controller 17 controlling the motor driver 16 to stop the five blowers 14, and then driving the pneumatic pollination device for hybrid rice seed production with a large row ratio to an agricultural machinery warehouse for maintenance as required, so as to prepare for pollination the next day.

Since the airflow velocity of each pollination pipe can be different, the airflow velocity at the air blowing port 21 of each pollination pipe is measured by the airflow velocity sensor 6 and adjusted by the blower 14 controlled by the motor driver 16 through the controller 17.

In addition, in the present application, five pollinators are used to blow and transport the pollen of six rows of male parents, or three pollinators are used for four rows of male parents, and seven pollinators correspond to eight rows of female parents.

The above is only a preferred embodiment of the present application, and is not used to limit the present application. Any slight modification, equivalent substitution and improvement made to the above embodiments according to the technical essence of the present application shall be included in the protection scope of the technical solution of the present application.

What is claimed is:

1. A pneumatic pollination device for hybrid rice seed production with a large row ratio, comprising a pneumatic pollination component, a controller, a lifting adjustment component, and a four-wheel power chassis, wherein the pneumatic pollination component is mounted at a front part of the four-wheel power chassis through the lifting adjustment component, the lifting adjustment component controls up-and-down lifting, and the controller is mounted at an upper part of the four-wheel power chassis;

wherein the pneumatic pollination component comprises a lifting frame, five airflow velocity sensors, a left side one-way pollination pipe, a left middle one-way pollination pipe, a central pollination pipe, a right middle one-way pollination pipe, a right side one-way pollination pipe, five blowers, five supporting plates, five motor drivers, and a storage battery;

wherein the left side one-way pollination pipe and the left middle one-way pollination pipe are both L-shaped, each of front parts of horizontal sections of the left side one-way pollination pipe and the left middle one-way pollination pipe is provided with an air blowing port on a side facing away from the central pollination pipe and a guide plate horizontally fixed below the air blowing port, and a base configured to install one of the five airflow velocity sensors is arranged at each of middle and lower parts of vertical sections of the left side one-way pollination pipe and the left middle one-way pollination pipe at a same height; the right side one-way pollinate pipe and the right middle one-way pollinating pipe are arranged in a mirror symmetrical structure with respect to the left side one-way pollinate pipe and the left middle one-way pollinating pipe, respectively;

wherein the central pollination pipe is also L-shaped, a front part of a horizontal section of the central pollination pipe is provided with two air blowing port at both sides of the front part, and the guide plate is horizontally fixed below each of the two air blowing port of the central pollination pipe; a middle and lower part of a vertical section of the central pollination pipe is provided with the base that is configured to install one of the five airflow velocity sensors, and an installation height of the base of the central pollination pipe is consistent with installation heights of the bases on the other pollination pipes;

wherein a rear part of a vertical part of each pollination pipe is provided with two L-shaped sliding sleeves, a distance between the two L-shaped sliding sleeves is consistent with a height of the lifting frame, and a locking bolt is arranged at an outer side of each of the two sliding sleeves; each pollination pipe is clamped and mounted at a front part of the lifting frame through the two L-shaped sliding sleeves and locked and fixed by the locking bolts, and lower parts of the horizontal sections of respective pollination pipes are located on a same horizontal plane;

wherein the five supporting plates are distributed and fixed at a rear upper part of a bracket, and one of the five blowers are fixed at a side of a respective one of the five supporting plates, and air inlets of the left side one-way pollination pipe, the left middle one-way pollination pipe, the central pollination pipe, the right middle one-way pollination pipe and the right side one-way pollination pipe are respectively connected with the five blowers through hoses;

wherein the five airflow velocity sensors are respectively fixed on the bases of vertical pipes of the left side one-way pollination pipe, the left middle one-way pollination pipe, the central pollination pipe, the right middle one-way pollination pipe and the right side one-way pollination pipe, and a measuring point of one of the five airflow velocity sensors extends to a center of the pollination pipe where the airflow velocity sensor is located; and wherein the storage battery is fixed on the four-wheel power chassis, the five motor drivers for airflow control are respectively fixed on the sides of the five supporting plates, a power input end of each of the five motor drivers is connected with the storage battery through a cable, and a power output end of each of the five motor drivers are connected with one of the five blowers through a cable; and control ends of the five motor drivers are connected with the controller through control cables.

2. The pneumatic pollination device for hybrid rice seed production with a large row ratio according to claim 1, wherein the lifting adjusting component comprises the bracket, two lifting guide rails, a sliding block, a screw rod, and a stepping motor;

a rear end of the bracket is fixed at the front part of the four-wheel power chassis, the two lifting guide rails are fixed at two sides of a front end of the bracket along a vertical direction, respectively; the sliding block is disposed at the lifting guide rails to form a moving pair, a rear part of the lifting frame is mounted on the lifting guide rails through the sliding block, and a middle and lower part of the screw rod is mounted at a middle part of the lifting frame through a ball nut; and an upper part of the screw rod is mounted on a front and upper middle part of the bracket through a bearing, the stepping motor is fixed on the front and upper middle part of the bracket, an upper end of the screw rod is fixedly connected with the stepping motor, a central axis of the screw rod is on a same line with an axis of an output shaft of the stepping motor, and the stepping motor drives the screw rod to rotate and drives the lifting frame to move up and down.

3. The pneumatic pollination device for hybrid rice seed production with a large row ratio according to claim 1, wherein vertical sections of the left side one-way pollination pipe, the left middle one-way pollination pipe, the central pollination pipe, the right middle one-way pollination pipe and the right side one-way pollination pipe have a same length; and the horizontal sections of the five pollination pipes are on a same plane, and a connecting line of centers of the front ends of the horizontal sections of the five pollination pipes is in a V-shape, which is concave toward the four-wheel power chassis.

4. The pneumatic pollination device for hybrid rice seed production with a large row ratio according to claim 3, wherein a length difference between the horizontal sections of two adjacent pollination pipes of the five pollination pipes is 1-1.5 times of a length of the air blowing port.

5. The pneumatic pollination device for hybrid rice seed production with a large row ratio according to claim 1, wherein the guide plate is in a triangular shape, and a tip of the guide plate faces a moving direction of the pneumatic pollination device hybrid rice seed production with a large row ratio.

6. The pneumatic pollination device for hybrid rice seed production with a large row ratio according to claim 1, wherein each of the air blowing ports of the five pollination pipes are arranged on a horizontal central plane of a respective one of the horizontal sections of the five pollination pipes.

7. A pollination method using the pneumatic pollination device for hybrid rice seed production with a large row ratio according to claim 2, comprising:

adjusting distribution of the pollination pipes: adjusting a horizontal position of the central pollination pipe on the lifting frame in such a manner that a longitudinal center of the central pollination pipe and a longitudinal center of the pneumatic pollination device for hybrid rice seed production with a large row ratio are located on a same vertical plane, and then fixing the central pollination pipe to the lifting frame through the locking bolts on the sliding sleeves; transversely and horizontally adjusting the left side one-way pollination pipe, the left middle one-way pollination pipe, the right middle one-way pollination pipe and the right side one-way pollination pipe based on a planting row spacing of male parents in such a manner that spacings of adjacent central lines of horizontal sections of the left side one-way pollination pipe, the left middle one-way pollination pipe, the central pollination pipe, the right middle one-way pollination pipe and the right side one-way pollination pipe are respectively consistent with five row spacings corresponding to six rows of male parents of hybrid rice in a seed production field, and then fixing each of the pollination pipes to the lifting frame by the locking bolts on the sliding sleeves;

moving the pneumatic pollination device to the seed production field: before 10:00 AM of a day during full bloom of the male parents of hybrid rice, driving the pneumatic pollination device for hybrid rice seed production with a large row ratio to the seed production field in such a manner that four walking driving wheels of the pneumatic pollination device straddle the six rows of male parents, wherein the four walking driving wheels are located between ridges of adjacent male and female parents of hybrid rice, and a horizontal section of the central pollination pipe is located between ridges of two rows of male parents at the utmost center among the six rows of male parents;

adjusting a height of the pneumatic pollination component: controlling, by the controller, the stepping motor to operate, the stepping motor driving a screw rod to rotate, and the screw rod driving the lifting frame to move up and down so as to drive the five pollination pipes to move up and down synchronously, and stopping movement of the five pollination pipes when the air blowing ports of the five pollination pipes reach the middle and lower parts of a spike region of the male parents;

adjusting airflow parameters of the pollination pipes: based on a requirement for pollination airflow velocity for a row of male parents of a current breed of hybrid rice, setting, by the controller, airflow velocities at the air blowing ports of the left side one-way pollination pipe, the left middle one-way pollination pipe, the central pollination pipe, the right middle one-way pollination pipe and the right side one-way pollination pipe, and then controlling, by the controller, the five motor drivers to drive the five blowers to operate, and outputting airflow at the air blowing ports of each of the pollination pipes at a preset wind speed;

pollinating field: during a period from 10:30 AM to 2:30 PM of a day when the male parents of hybrid rice are in full bloom, after adjusting the airflow parameters of the pollination pipes, the pneumatic pollination device for hybrid rice seed production with a large row ratio straddling six rows of the male parents of hybrid rice and advancing along a center line at a specified speed, the left side one-way pollination pipe, the left middle one-way pollination pipe, the central pollination pipe, the right middle one-way pollination pipe and the right side one-way pollination pipe respectively being located between rows of the six rows of the male parents of hybrid rice, blowing airflow from the air blowing ports of the left side one-way pollination pipe and the left middle one-way pollination pipe to spike parts of the left two rows of the male parents, blowing airflow from the air blowing ports of the right middle one-way pollination pipe and the right side one-way pollination pipe to spike parts of the right two rows of the male parents, and blowing airflow from the air blowing ports of the two sides of the central pollination pipe to spike parts of the central two rows of the male parents respectively; pollens of the male parents being separated from flower cores and floating with the airflow under the action of airflow and spike swing, pollens of the left three rows of male parents floating to the left adjacent row of female parents under the action of left-ward airflow, and pollens of the right three rows of male parents floating to the right adjacent row of female parents under the action of right-ward airflow; with the gradual decrease of the airflow velocity above a female parent compartment, pollens settling down under the action of gravity, and part of the pollens settling on the spike parts of the female parents to realize pollination; when the pneumatic pollination device for hybrid rice seed production with a large row ratio travels to an end point of the six rows of male parents in the compartment, the pneumatic pollination device turning around in the field to the six rows of the male parents in another adjacent compartment to continue pollination; and the pneumatic pollination device traveling to each male parent compartment in turn for pollination, and performing pollination 2-3 times a day from 10:30 AM to 2:30 PM of a day during the full bloom; and stopping maintenance: after pollination is finished every day, firstly controlling, by the controller, the motor drivers to stop the five blowers, and then driving the pneumatic pollination device for hybrid rice seed production with a large row ratio to an agricultural machinery warehouse for maintenance, so as to prepare for pollination of the next day.

8. The pollination method according to claim 7, wherein the airflow velocities of the pollination pipes are different from each other, and the airflow velocity at the air blowing port of each of the pollination pipes is measured by one of the five airflow velocity sensor and adjusted by the one of the five blowers that is controlled by the motor driver through the controller.

* * * * *